United States Patent [19]

Cumming

[11] Patent Number: 5,562,731
[45] Date of Patent: Oct. 8, 1996

[54] INTRAOCULAR IMPLANT METHODS

[76] Inventor: J. Stuart Cumming, #201 - 1211 W. LaPalma Ave., Anaheim, Calif. 92801

[21] Appl. No.: 268,794

[22] Filed: Jul. 1, 1994

Related U.S. Application Data

[62] Division of Ser. No. 744,472, Aug. 12, 1991, Pat. No. 5,326,347.

[51] Int. Cl.$^6$ ........................................ A61F 2/16
[52] U.S. Cl. ........................................ 623/6
[58] Field of Search ........................................ 623/6

[56] References Cited

U.S. PATENT DOCUMENTS

| | | | |
|---|---|---|---|
| 4,888,016 | 12/1989 | Langerman | 623/6 |
| 4,932,971 | 6/1990 | Kelman | 623/6 |
| 4,963,148 | 10/1990 | Sulc et al. | 623/6 |
| 5,074,876 | 12/1991 | Kelman | 623/6 |
| 5,203,788 | 4/1993 | Wiley | 623/6 |

Primary Examiner—Randy C. Shay
Attorney, Agent, or Firm—Boniard I. Brown

[57] ABSTRACT

An intraocular implant for use in a human eye following cataract, refractive or other eye surgery. The implant has a holder and imaging optics which may be folded to a compact configuration, inserted into the eye separately, and then assembled by the surgeon in the eye by mounting the optics on the holder after the holder has been implanted in the eye. These optics include a lens which is adjustable within the eye relative to the holder by the surgeon during surgery to focus the optics on the retina of the eye and are adjustable postoperatively by the implantee to near and distant focus positions by movement of the implantee's head and by magnetic action. The disclosed implants are inserted into the capsular bag of an eye from which the nucleus and cortex have been removed and retain the bag in substantially its natural shape and volume in a manner which inhibits opacification of the posterior capsule of the bag, prevents the vitreous volume from increasing postoperatively, and thereby prevents many complications which often attend cataract surgery.

16 Claims, 6 Drawing Sheets

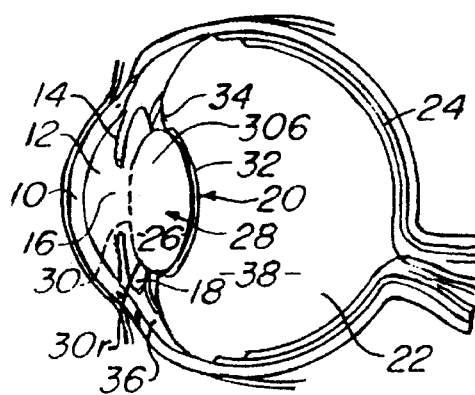
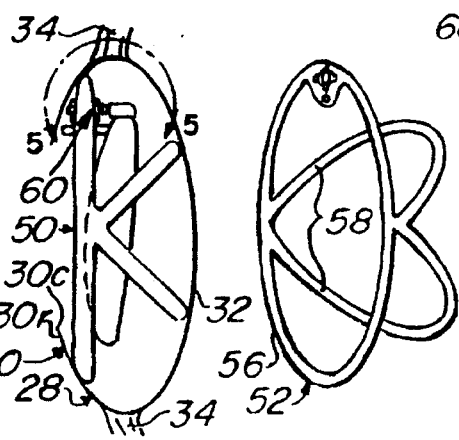
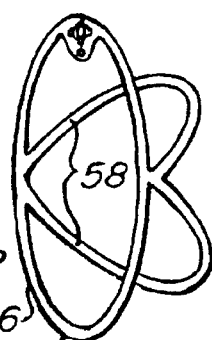
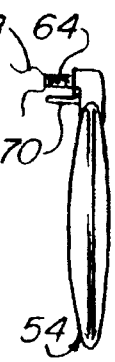
FIG-1   FIG-2   FIG-3   FIG-4
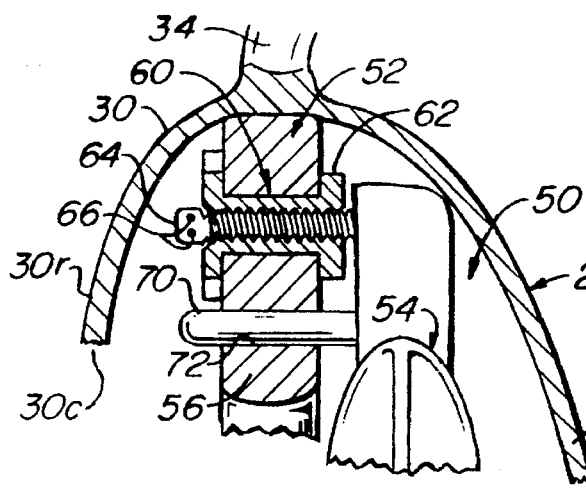
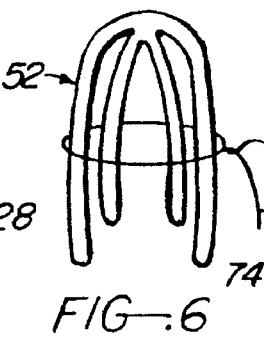
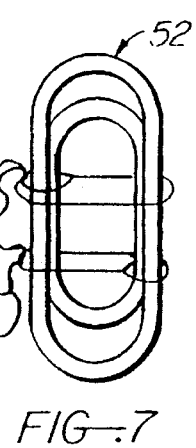
FIG-5   FIG-6   FIG-7
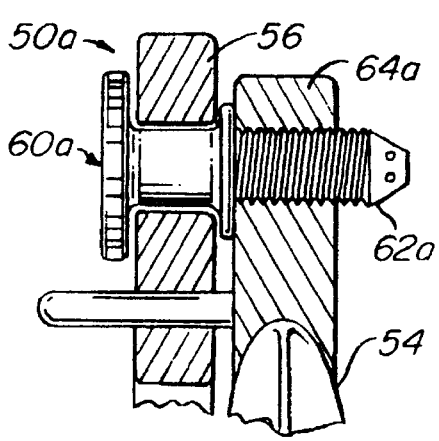
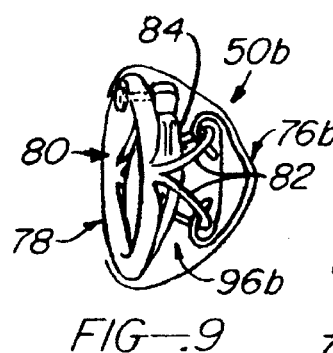
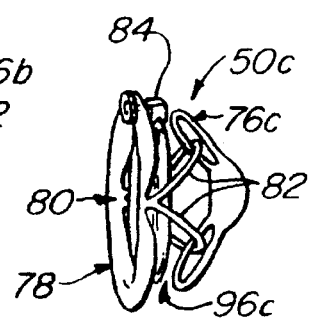
FIG-8   FIG-9   FIG-10

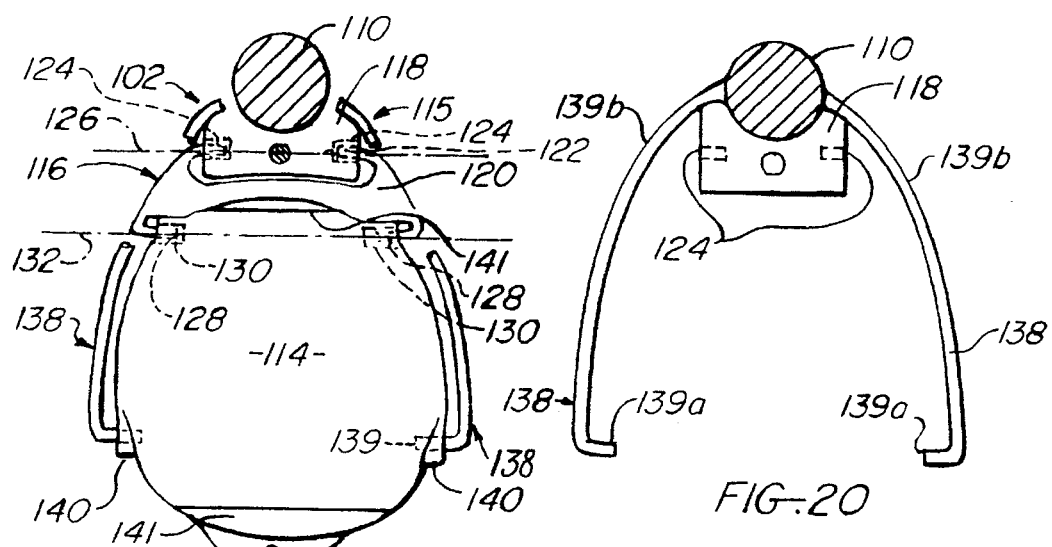
FIG-18
FIG-20
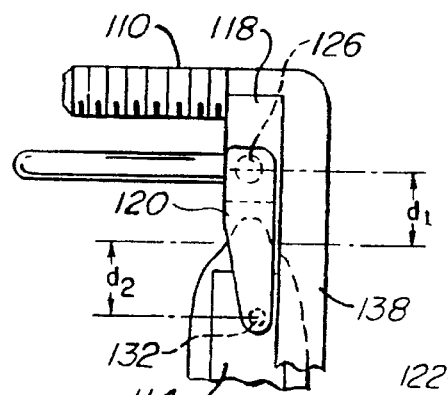
FIG-18A
FIG-20A
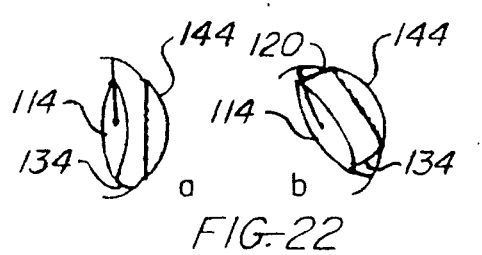
FIG-22
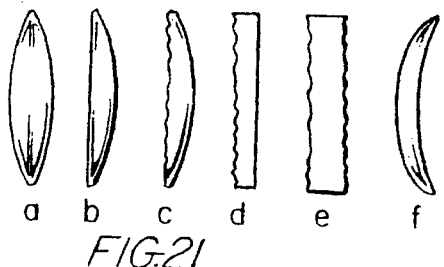
FIG-21
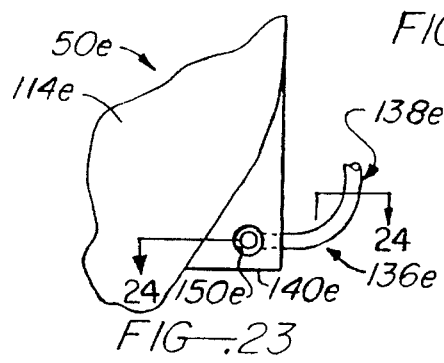
FIG-23
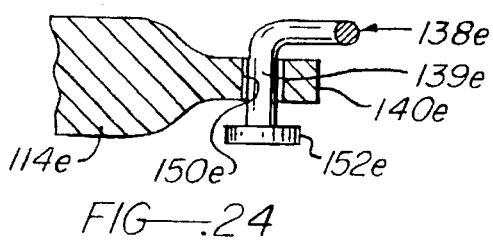
FIG-24

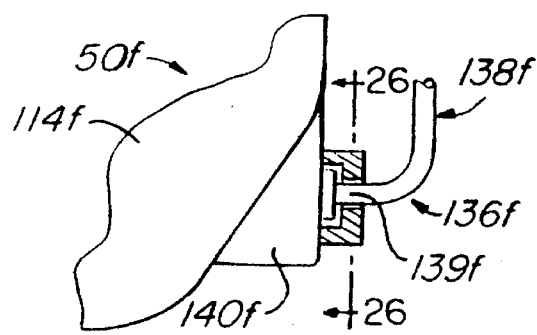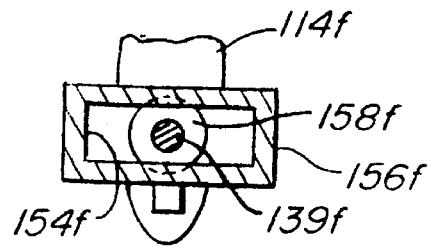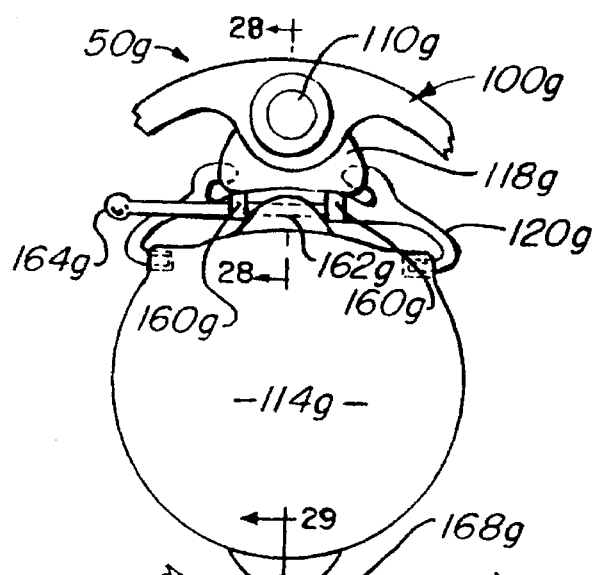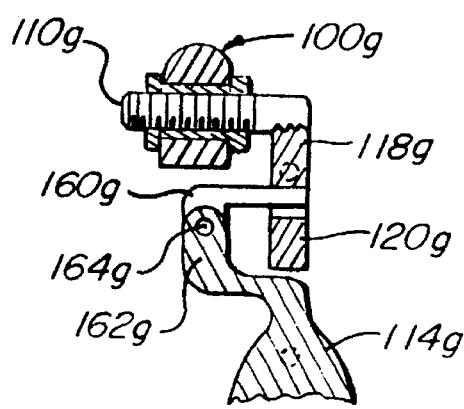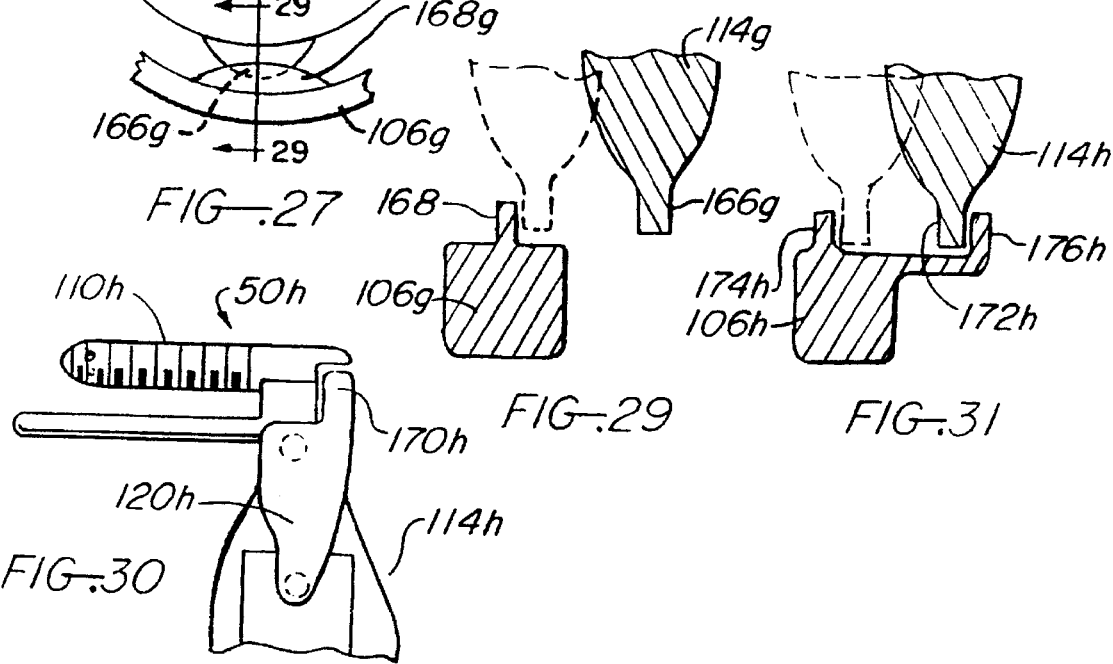

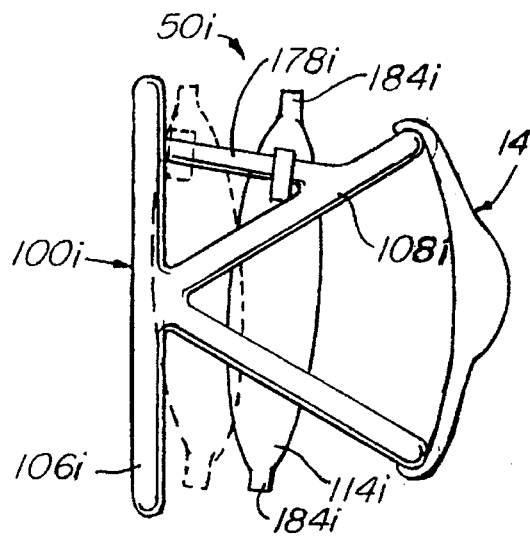
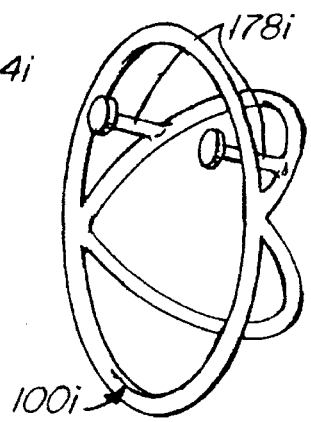
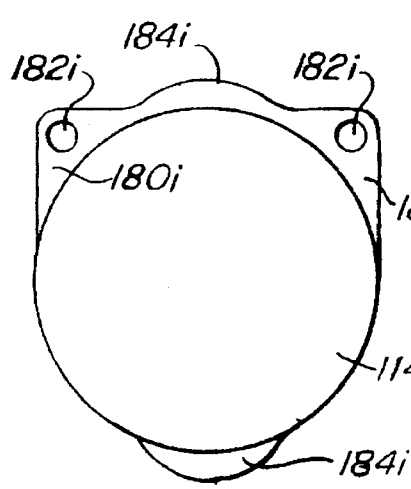
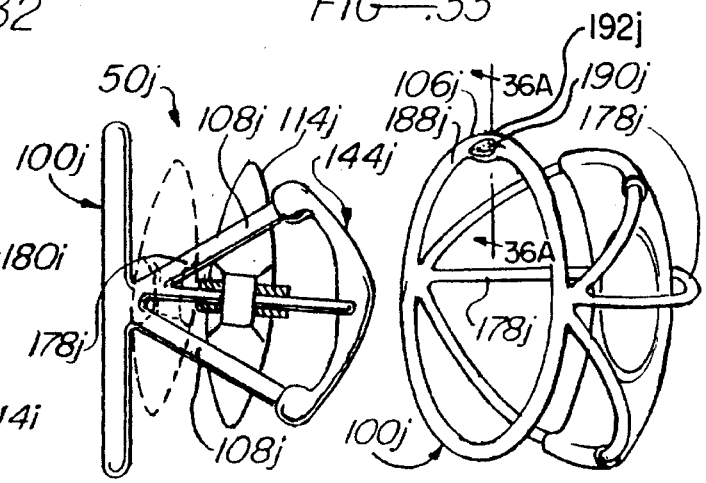
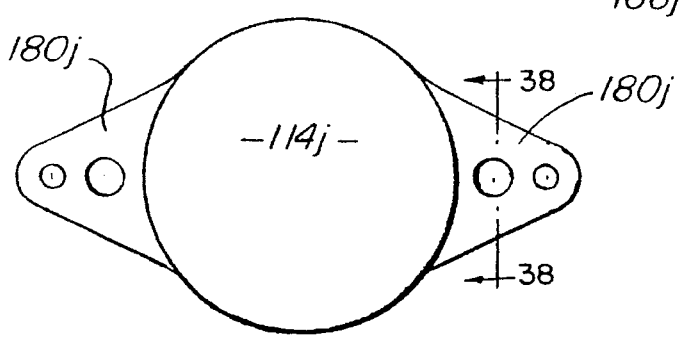
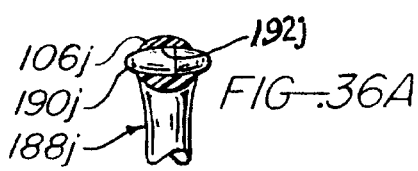
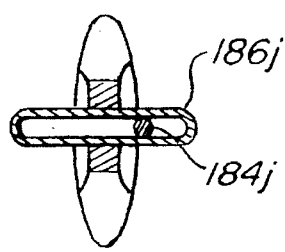

INTRAOCULAR IMPLANT METHODS

RELATED APPLICATION:

This application is a division of prior application Ser. No. 07/744,472, filed Aug. 12, 1991, now U. S. Pat. No. 5,326,347.

BACKGROUND OF THE INVENTION

1. Field of the Invention

This invention relates generally to intraocular correction of human vision disorders and more particularly to novel intraocular implants and methods for this purpose.

2. Prior Art

The human eye is commonly regarded as comprising an outer anterior transparent cornea, an iris behind the cornea which contains the pupil and forms with the cornea an intervening anterior chamber, a lens behind the iris which forms with the iris an intervening posterior chamber, and a retina at the rear of the eye on which entering light rays are focussed by the lens and which forms with the lens an intervening vitreous chamber containing vitreous. The natural lens of the eye comprises a transparent envelope, called a capsular bag, which contains a crystalline structure and is suspended by zonules from the surrounding ciliary body. The front and rear walls of the capsular bag are known as anterior and posterior capsules, respectively.

One of the eye abnormalities or disorders that seriously affects vision is a cataract which is a condition of the natural lens of the human eye characterized by progressive opacification of the lens. A cataractous eye condition is corrected or cured by surgical removal of the cataractous lens material through an incision in the cornea. In the early days, cataract surgery involved removal of the entire cataractous lens, i.e. both the inner lens structure and the outer capsulary bag. The artificial lenses used to replace the removed human lens were thick external "cataract lenses" worn as glasses.

Shortly after World War II, a British ophthalmic surgeon by the name of Harold Ridley implanted, for the first time, an artificial lens, referred to as an intraocular lens or lens implant, directly within a patient's eye to replace the surgically removed natural lens. Since that time, cataract surgical techniques and intraocular lens implants have progressed enormously. The great advantage of intraocular lens implants, of course, resides in the fact that they eliminate the need to wear thick cataract glasses which distort vision and are uncomfortable to wear because of their weight.

Many different cataract removal and intraocular lens implanting techniques and intraocular lens implant designs have been developed over the years since the first lens implant by Ridley. Two older cataract removal techniques may be categorized generally as intracapsular cataract extraction and extracapsular cataract extraction. In the intracapsular extraction technique, the entire natural lens, including the inner lens structure and outer capsulary bag, are removed. In the extracapsular technique, the inner lens structure is removed through an anterior opening in the capsular bag, created by either incising or removing the anterior capsule of the bag, and the posterior capsule of the bag is left intact.

A great variety of intraocular lens implants have been developed. Examples of the existing intraocular implants are disclosed in the following U.S. Pat. Nos.: 4,298,996; 4,435,856; 4,573,998; 4,673,406; 4,730,286; 4,753,655; 4,813,955; 4,994,082; 4,424,587; 4,738,680; 4,842,601; EP-162-573-A (European). The implants disclosed in U.S. Pat. Nos. 4,435,856; 4,573,998; 4,813,955; 4,994,082; EP-162-573-A are adjustable by gravity, magnets, inflation, ciliary muscle action, or otherwise for near and distant vision accommodation. The implants disclosed in U.S. Pat. Nos. 4,435,856; 4,573,998; 4,753,655; EP-162-573-A have multiple lens systems. The lenses in U.S. Pat. No. 4,573,998 are foldable to minimize the size of the corneal incision through which the lenses are inserted into the eye. U.S. Pat. Nos. 4,424,597, 4,738,680, and 4,842,601 disclose intraocular lenses which are implanted in a patient's eye following extracapsular extraction of the natural lens matrix and bear against the remaining natural posterior capsule in the eye. The lenses in some patents are bifocal lenses or are optically conditioned to focus less than 50% of the light from near objects and less than 50% of the light from far objects onto the retina simultaneously. Some light is lost. The brain has then to select which image it wishes to recognize, the near image or the far image.

Cataract surgery techniques and intraocular lens implants such as those described in the above patents give rise to certain complications. The major complications in this regard are opacification of the posterior capsule when extracapsular cataract extraction is utilized, intraocular lens decentration, cystoid macular edema, retinal detachment, and astigmatism. In the late 1980's an improved surgical technique referred to as continuous tear circular capsulotomy, more technically as capsulorhexis, was developed for use in cataract surgery applications. This improved technique reduces the complications associated with such surgery, particulary lens decentration.

Simply stated, capsulorhexis involves tearing a generally circular opening (capsulotomy) through the anterior capsule of the capsular bag. This opening or capsulotomy is bounded circumferentially by an annular remnant of the anterior capsule. This annular remnant of the anterior capsule provides a continuous annular rim about the capsulotomy which forms with the posterior capsule a capsular bag. During a cataract operation, the cataractous nucleus and cortex of the natural lens is removed from the capsular bag and an artificial lens implant is inserted into the bag through this capsulotomy. U.S. Pat. Nos. 4,409,691 and 4,842,601 disclose intraocular lenses implanted within a capsular bag. The capsular bag in U.S. Pat. No. 4,409,691 appears to have an anterior circular capsulotomy.

Up to the present time, capsulorhexis has been used with conventional lens implants having haptics or the like. A unique advantage of capsulorhexis resides in the fact that fibrosis during healing-tends to effectively "shrink wrap" the capsular bag about the lens implant in such a way as to firmly retain the implant in position postoperatively.

While capsulorhexis is effective to reduce or eliminate some of the cataract surgery complications referred to above, such as lens decentration, the existing intraocular lens implants used with this and other cataract surgery techniques have certain deficiencies which this invention alleviates or eliminates. Among the foremost of these deficiencies to which some or all of the prior implants are subject are the following. Prior intraocular lenses which are either designed for or are capable of implantation in a capsular bag with an anterior capsulorhexis do not preserve the natural shape and volume of the bag and hence do not preserve the natural vitreous volume of the eye. Wile some of these lens implants may reduce some postoperative opacification of the posterior capsule of the bag, they still permit at least some opacification which is undesirable and which, ideally, should be further reduced or eliminated.

There are currently no known practical methods or intraocular implants which guarantee the patient excellent postoperative uncorrected visual acuity, particularly with intraocular multifocal lens implants. For example, the prior intraocular lenses do not permit refracting a patient and focusing the intraocular lens on the retina of the patient's eye during the actual surgery. As is evident from the prior patents listed above, adjustable intraocular lenses have been devised, but these are not designed for focusing adjustment within the eye during surgery. Some prior intraocular lenses are foldable to reduce the size of the incision required for insertion of the lens into the eye, but these lenses are not capable of focusing adjustment within the eye during surgery. Although the prior patents listed above do disclose intraocular lenses which allege near vision and far vision accommodation capability by ciliary muscle action or other action of the patient, there are, to my knowlege, no practical accommodating intraocular lenses currently available to the ophthalmic surgeon.

SUMMARY OF THE INVENTION

This invention provides improved intraocular implants and methods which avoid the above noted and other deficiencies of the existing intraocular lenses. It should be noted at the outset that the invention is particularly concerned with and will be described primarily in connection with cataract surgery involving the creation of a space in front of the vitreous, behind the iris, and within the capsular bag by extracapsular extraction of the opacified or cataractous natural lens cortex and nucleus through an anterior circular capsulotomy in the bag and implantation of an intraocular lens in the bag through the circular capsulotomy. As will appear from the later description, however, the invention may be utilized in any one of the eye chambers, i.e. anterior chamber, posterior chamber, or vitreous chamber, and in other than cataract surgical applications. For example, the invention may be utilized to correct a refractive error, to provide a patient with accommodation, and to restore accommodation to those in the presbyopic age group.

According to one of its aspects, the invention provides an intraocular lens implant which is adapted to be implanted within the capsular bag of a patient's eye after removal of the bag contents, either by planned extracapsular extraction or phacoemulsification of the contents. The implant maintains the capsular bag in a permanent post-operative configuration conforming closely in shape and volume to the natural preoperative shape and volume of the bag. The implant lens is optically designed to focus entering light rays on the retina of the eye. Because it maintains the natural shape and volume of the capsulary bag, the implant also preserves substantially the natural vitreous volume of the eye and thereby virtually eliminates the complications of cystoid macular edema and retinal detachment.

The preferred implant is foldable to a compact folded configuration to reduce the size of the incision required for insertion of the implant into the eye and is particularly suited for insertion into a capsular bag having an anterior capsulotomy. When released within the eye, the implant slowly unfolds or expands to its normal inplant configuration to maintain the capsular bag in its normal size and shape. Certain preferred implants of the invention include a posterior capsule stretcher which presses firmly against the posterior capsule of the capsular bag, stretching it and inhibiting opacification of this capsule. The posterior capsule stretcher also permits a central portion of an opacified posterior capsule to be surgically removed in order to preserve or restore a patient's vision since the stretcher and posterior capsule engage in sealing relation about the resulting posterior capsule opening to prevent vitreous leakage from the vitreous chamber into the capsular bag.

According to another aspect of the invention, the intraocular implant includes a lens holder and a lens mounted on the holder. The preferred implants are designed for implantation within a capsular bag, and their lens holders retain substantially the natural shape and volume of the capsular bag. In one disclosed implant, the lens holder is a relatively open cage-like structure including arcuate limbs which press against the posterior capsule and the remaining anterior capsule rim of the capsulary bag to preserve its normal shape and volume. The lens is mounted within this cage. In another disclosed implant, the lens holder is a balloon. A unique feature of certain of these preferred embodiments resides in the fact that the lens holder and lens(es) are adapted for insertion into the eye separately and then assembled within the eye by the surgeon. At least the holder, and in some cases other parts of the implant, are preferably foldable to a compact configuration for insertion into the eye. Another, particularly important and beneficial feature of certain preferred inventive embodiments resides in the fact a lens of the implant is adjustably mounted on the lens holder in a manner which permits the surgeon to refract a patient and adjust the lens to precisely focus the lens on the retina of the eye, all during surgery. This feature ritually guarantees the patient excellent postoperative uncorrected visual acuity even when the intraocular implant lens is a multifocal lens.

The invention also provides intraocular lens implants which have accommodation capability, that is, the ability to adjust for near and distant vision. This accommodation is exercised, in some disclosed embodiments, by head movement, in other embodiments by ciliary muscle action, and in some embodiments by magnetic action. The invention also contemplates within its scope the use of lenses or other optical elements which are optically conditioned to transmit only certain wavelengths of light, multiple lens implants, and implants with either or both spherical, planar, and Fresnel lens surfaces.

According to another important feature of the invention, the implant includes an opthalmic drug dispenser, such as a time release capsule, for dispensing a controlled dosage of an opthalmic drug into the eye over an extended period of time. The invention also provides an multioptic intraocular lens system which functions, by itself or in combination with an external lens in the form of a spectacle lens, contact lens, or another intraocular lens, as a telescopic magnifying system for magnifying images on the retina of a person with macular degeneration, thus enabling the person to see.

BRIEF DESCRIPTION OF THE DRAWINGS

FIG. 1 is a section through the human eye;

FIG. 2 illustrates an intraocular implant according to this invention implanted within the capsular bag of a human eye;

FIG. 3 is a perspective view of a lens holder embodied in the implant of FIG. 2;

FIG. 4 is a perspective view of a lens embodied in the implant of FIG. 2;

FIG. 5 is an enlarged section through the portion of the implant encircled by the arrow 5—5 in FIG. 2;

FIGS. 6 and 7 illustrate two ways of folding the lens holder of FIGS. 2–5 to a compact configuration for insertion through a small incision into the capsular bag in FIG. 2;

FIG. 8 is a fragmentary section through a modified intraocular implant according to the invention;

FIG. 9 is a perspective view of a further modified intraocular implant according to the invention;

FIG. 10 is a perspective view of a further modified intraocular implant according to the invention;

FIG. 18 is an anterior section on line 18—18 in FIG. 17 illustrating an adjustable, accommodating lens assembly embodied in the implant of FIG. 17;

FIG. 18A is an enlarged fragmentary side elevation of the lens assembly in FIG. 18;

FIG. 20 is an enlarged section taken on line 20—20 in FIG. 19;

FIG. 20A is a view of the anterior side of another component of the lens assembly in FIG. 18;

FIG. 21 illustrates several possible optical shapes of the lens in the implant of FIGS. 17–20;

FIG. 22 diagrammatically illustrates the accommodating action of the implant in FIGS. 17–20;

FIG. 23 is an enlarged fragmentary view of a modified intraocular implant according to the invention;

FIG. 24 is a section taken on line 24—24 in FIG. 23;

FIG. 25 is an enlarged fragmentary view similar to FIG. 23 and partly in section of a further modified intraocular implant according to the invention;

FIG. 26 is a section taken on line 26—26 in FIG. 25;

FIG. 27 is a fragmentary view of the anterior side of a further accommodating intraocular implant according to the invention;

FIG. 28 is a section taken on line 28—28 in FIG. 27;

FIG. 29 is a section taken on line 29—29 in FIG. 27;

FIG. 30 is a fragmentary side elevation of the accommodating lens assembly of a further modified accommodating intraocular implant according to the invention;

FIG. 31 is a section similar to FIG. 29 through an implant embodying the lens assembly of FIG. 30;

FIG. 32 is a side elevation of a further modified accommodating intraocular implant according to the invention;

FIG. 33 is a perspective view of a lens holder embodied in the implant of FIG. 32;

FIG. 34 is a view of the anterior side of a lens embodied in the implant of FIG. 32;

FIG. 35 is a side elevation of a further modified accommodating intraocular implant according to the invention;

FIG. 36 is a perspective view of a lens holder and posterior capsule stretcher embodied in the implant of FIG. 35;

FIG. 36A is an enlarged section taken on line 36A—36A of FIG. 36 illustrating a time release ophthalmic drug dispenser embodied in the implant;

FIG. 37 is a view of the anterior side of a lens embodied in the implant of FIG. 35;

FIG. 38 is a section taken on line 38—38 in FIG. 37;

DESCRIPTION OF THE PREFERRED EMBODIMENTS

Figure 11:
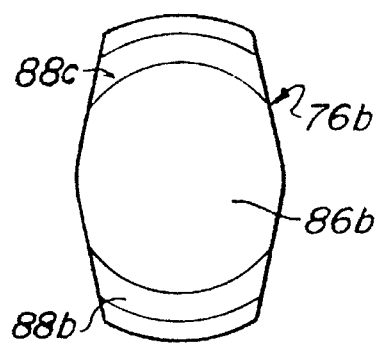
FIG. 11 is an enlarged view of a posterior capsule stretcher embodied in the implant of FIG. 9.
Figure 12:
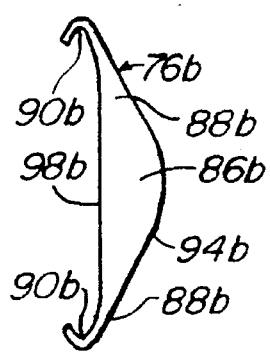
FIG. 12 is side view of the posterior capsule stretcher in FIG. 11.
Figure 13:
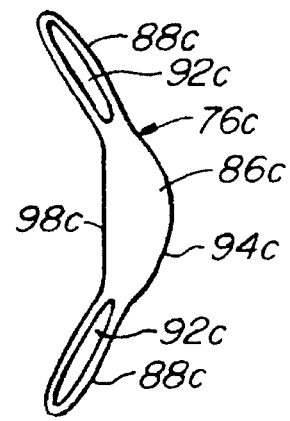
FIG. 13 is an enlarged side elevation similar to FIG. 12 of a posterior capsule stretcher embodied in the implant of FIG. 10.
Figure 14:
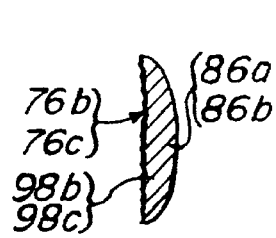
FIGS. 14–16 are sections illustrating different optical configurations to which an optical portion of the posterior capsule stretchers in FIGS. 9 and 10 may conform.
Figure 15:
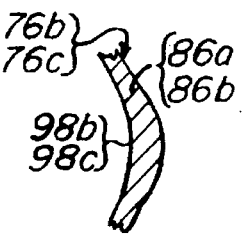
Figure 16:
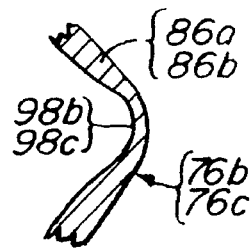

Turning now to these drawings and first to FIG. 1 for reference in the ensuing description, the human eye comprises from front to rear an outer transparent cornea 10, an anterior chamber 12, an iris 14 containing a pupil 16, a posterior chamber 18, a natural lens 20, a vitreous cavity 22, and a retina 24. The natural lens 20 comprises a crystalline lens structure 26 contained within an optically clear bag called a lens capsule 28 having an anterior capsule 30 and a posterior capsule 32. The lens is peripherally joined by zonules 34 to the surrounding ciliary muscles 36. The vitreous cavity 22 contains vitreous 38.

As mentioned earlier, the invention is concerned primarily with correcting the eye disorder known as a cataract which is characterized by progressive opacification of the natural lens 20 and resultant progressive attenuation of the light rays reaching the retina. Simply stated, this condition is corrected by removing the cataract, that is the cataractous nucleous and cortex of the natural lens, and implanting an artificial intraocular lens in the eye. Cataract removal may be accomplished by intracapsular extraction (removal of the entire lens 20) or by extracapsular extraction (removal of the cataractous nucleus and cortex through the anterior side of the lens capsule bag 28) utilizing either nucleus expression and a relatively large opening in the eye or phacoemulsification and a relatively small opening in the eye.

The anterior capsule opening required for extracapsular extraction may be provided by (a) removing most of the anterior capsule 30 except possibly small peripheral remanents of the anterior capsule, (b) tearing the anterior capsule to allow the human lens nucleus to be expressed, or (c) continuous tear circular capsulotomy, i.e. capsulorhexis. The essentially empty lens capsule 28 remaining after removal of the cataract is referred to as a capsular bag. Removal of the nucleus and cortex of the natural lens from the bag creates a space immediately behind the iris 14, between the latter and the posterior capsule 32 of the bag, which is approximately 10 mm in diameter and 5 mm front to back.

As is evident from the prior patents listed earlier, it is possible to implant an intraocular lens in any one or more of the eye chambers, i.e. anterior chamber 12, posterior chamber 18, capsular bag 28, or vitreous cavity 22. Intraocular implants according to this invention may be placed in any one of these eye chambers or cavities. However, the invention is particularly concerned with intraocular implants for placement in a capsular bag having a circular anterior capsulotomy and will be described primarily in this context.

Referring now to FIGS. 2–5, there is illustrated an intraocular implant 50 according to the invention within a capsular bag 28 of the human eye from which the nucleus and cortex of the natural lens has been removed. The capsular bag 28 has an anterior circular capsulotomy 30C through which the implant is inserted into the bag. This capsulotomy leaves intact on the capsular bag 28 a remanent of the anterior capsule 30 in the form of an annular lip or rim 30R about the capsulotomy. The implant 50 includes a lens holder 52 having a normally anterior/posterior direction and anterior and posterior sides from one another in this direction to form a space between the sides and an artificial refractor or lens 54 mounted on the holder within this space. The particular lens holder shown is a generally open cage-like structure including a base ring 56 which forms the anterior side of the holder and arcuate limbs 58 projecting rearwardly from the normally posterior side of the ring and forming the posterior side of the holder. The holder or cage has a anterior/posterior direction or axis normal to the plane of the ring. The limbs 58 have ends integrally joined to the base ring 56 at diametrically opposite positions about the ring and extend posteriorly from the ring in divergent planes, as shown. The lens 54 is situated immediately behind the holder base ring 56, within the anterior portion of the holder space, and is secured to the base ring 56 by mounting means 60 with the plane of the lens substantially parallel to the plane of the base ring. As shown in the drawings, the anterior/posterior dimension of the space within the lens holder is substantially greater than the thickness dimension of the lens along its optic axis, and the diameter of the holder base ring is greater than the diameter of the lens. The space within the lens holder is thereby sized to receive the lens in the anterior portion of the holder space and to accommodate adjustment of the lens relative to the holder in the anterior/posterior direction of the holder without projection of the lens beyond the anterior and posterior sides of the holder in the anterior/posterior direction of the holder and without projection of the lens beyond the anterior end of the holder in a direction transverse to the anterior/posterior direction or axis of the holder, i.e. without projection of the lens beyond the base ring of the holder in the radial direction of the ring.

According to a preferred feature of the invention, mounting means 60 is releasable to permit separation of the lens 54 from the lens holder cage 52 for insertion of the cage and lens into the capsular bag 28 separately and attachment of the lens to the cage within the bag by the surgeon during surgery after the cage has been properly implanted in the bag. To this end, the mounting means 60 comprises coacting mounting members 62, 64 on the cage and lens, respectively, which are initially separated or disengaged to permit insertion of the cage and lens into the eye separately and are engagable by the surgeon during surgery after the cage has been implanted within the capsular bag. In FIGS. 1–5, the cage mounting member 62 is an internally screw threaded sleeve-like nut journalled within and restrained against axial movement relative to an enlarged portion of the base ring 56 for rotation of the nut on an axis transverse to the plane of the ring. The anterior end of nut 62 is shaped in any appropriate way, such as that shown in FIG. 3, to permit rotation of the nut relative to base ring 56 by the surgeon during surgery. The lens mounting member 64 is a screw joined to the lens 54 and sized to be threaded into the cage nut 62.

The anterior end of the lens mounting screw 64 has holes 66 to receive a surgical thread 68 for aiding engagement of the screw in the cage nut 62 during surgery after the cage 52 has been implanted within the capsular bag 28. The surgeon inserts this thread through the nut 62 of the implanted cage 52 from the posterior end of the nut and then pulls on the thread to pull the lens mounting screw 64 into the posterior end of the nut. The nut is then rotated by the surgeon to engage the screw in the nut. The lens 54 also mounts a guide pin 70 which parallels and extends axially a short distance beyond the end of the screw and is slidable within a guide bore 72 in the cage base ring 56 parallel to the axis of the nut 62. This guide pin serves several purposes, namely guiding the screw 64 into the nut 62 during assembly of the lens 54 on the cage 52, preventing rotation of the lens with the nut during rotation of the nut to connect the lens to the cage, and retaining the lens in a fixed angular position about the axis of the screw and nut relative to the cage. When thus mounted on the cage 52, the lens 54 is contained within the interior space of the cage in substantially coaxial alignment with the cage base ring 56 and with the plane of the lens substantially parallel to the plane of the base ring. The lens is adjustable within the cage, parallel to the axis of the nut 62 and screw 64 by rotation of the nut.

After the cataractous nucleus and cortex of the natural lens 26 has been removed from the lens capsule or capular bag 28 through the circular capsulotomy 30C during cataract surgery, the lens holder or cage 52 is inserted into the bag through the capsulotomy and is implanted in the bag approximately in the fixed implanted position shown in FIG. 2. In this implanted position the cage is located between the capsular rim 30R and the posterior capsule 32, the anterior/posterior direction or axis of the cage generally parallels the axis of the eye, the base ring 56 of the cage seats in the internal annular crevice-like space or cul-de-sac which exists at the juncture of the anterior capsule rim 30R and the posterior capsule 32, and the cage limbs 58 press rearwardly against the posterior capsule 32. In some cases, it may be desirable or necessary to condition the capsular bag to receive the cage between its anterior rim 30R and posterior capsule 32 by filling the bag with a visco-elastic material in order to balloon the bag outwardly to its natural shape and displace the floppy posterior capsule 32 of the bag rearwardly to its natural position. This visco-elastic material is removed at conclusion of the surgery. After the cage 52 has thus been implanted in the capsular bag 28, the lens 54 is inserted into the bag to its illustrated position within the interior of the cage at the rear of the cage base ring 56, and the lens mounting screw 64 is engaged in the cage nut 62 in the manner explained above to mount the lens on the cage.

The implant cage 52 is sized and shaped so that when it is implanted in the capsular bag 28, engagement of the cage limbs 58 with the posterior capsule 32 of the bag maintains the bag in a postoperative configuration conforming closely to its natural size and shape. This preservation of the natural size and shape of the capsular bag prevents the vitreous volume in the vitreous cavity 22 from increasing postoperatively. The normal cataract surgery complications of cystoid macular edema and retinal detachment are thereby virtually eliminated. The implant cage 52 is an essentially open structure which permits light rays that enter the eye to pass through the cage openings to the retina 24. The intraocular implant 50 is constructed and arranged in such a way that the lens 54, when mounted on the implanted cage 52, is optically aligned with the optic axis of the eye to focus these entering light rays on the retina.

A particularly important and useful feature of the intraocular implant 50 resides in the fact that after the intraocular lens device 50 has been implanted in the eye, but before the surgery is completed, the surgeon may refract the patient and adjust the lens 54 toward and away from the retina 24 by rotating the cage nut 62 to accurately focus the lens on the retina. The cage 52 provides the space within the capsular bag 28 necessary for this adjustment. After adjustment, the lens is fixed in its focused position in any convenient way. This lens adjustment during surgery guarantees the patient excellent uncorrected postoperative visual acuity. In a preferred implant according to the invention, the mating threads on the nut 62 and screw 64 will be designed to change the power of the lens 1 Diopter with each 360 degree rotation of the nut. It is envisioned that a set of lenses for possible use in the implant will range in power from +10 to +26 Diopters in 0.5 Diopter increments. The lens for a particular patient will be selected from this set and then fine tuned to the patient by adjustment of the lens in the manner explained above. The patient lies on his back with the lens horizontal during such refraction and focussing of the lens. In the particular implant illustrated, the lens 54 is rigid on the screw 64 and thus remains horizontal during the refracting and focussing procedure.

According to a preferred feature of the invention, at least the implant cage 52 is constructed of an inert foldable material having elastic memory to permit the cage to be folded to a compact configuration for insertion into the eye through a small incision and then released within the eye to unfold or expand slowly by stored elastic strain energy to the normal implant configuration of FIGS. 2–5. FIGS. 6 and 7 illustrate two possible ways of thus folding the cage 52. The cage may be retained in its folded configuration in any convenient way during its insertion into the eye. For example, the folded cage may be bound with ties 74 which can be cut after insertion of the cage to release the cage for expansion within the eye. Exemplary foldable cage materials are PROLENE, methyl methacrylate, titanium, platinum, polyamide, and the like. The ability of the cage 52 and lens 54 to be inserted into the eye separately and then reassembled by the surgeon within the eye, as explained above, constitutes another important feature of the invention which permits more compact folding of the cage than would be possible if the lens remained attached to the cage.

FIG. 8 illustrates a modified intraocular implant 50a according to the invention including modified lens mounting means 60a which effectively reverse the positions of the lens mounting nut 62 and screw 64 in FIGS. 2–5. Thus, in FIG. 8, the cage mounting member 62a comprises a screw rotatable in the cage, and the lens mounting member 64a comprises a threaded nut rigid on the lens and threadedly receiving the cage screw. The screw is rotatable by the surgeon to adjust the lens in much the same manner as the nut 62 in FIGS. 2–5 is rotated to adjust the lens.

Attention is now directed to FIGS. 9–16 illustrating two modified intraocular implants 50b, 50c according to the invention. Each of these modified intraocular implants comprises a posterior capsule stretcher, identified as 76b in FIG. 9 and as 76c in FIG. 10, mounted on an implant assembly 78. This implant assembly may be identical to the implant 50 in FIGS. 2–5 or the implant 50a in FIG. 8 and hence need not be redescribed in detail. Suffice it to say that the implant assembly 78 includes a lens holder or cage 80 having arcuate posterior limbs 82 and a lens 84 mounted on the cage. The posterior capsule stretchers 76b, 76c have central transparent optical portions 86b, 86c, respectively, and haptics 88b, 88c at diametrically opposite sides of the optical portions. Haptics extend outwardly and rearwardly from the optical portions at an oblique angle to the axis of the optical portions and are attached to the limbs 82 of the respective implant assembly cage 80 in a position such that the optical portion of each posterior capsule stretcher is optically aligned with the respective implant assembly lens 84.

The haptics 88b of the posterior capsule stretcher 76b have outer generally hook-shaped ends forming posterior channels 90b in the haptics which receive the rear arcuate extremities of the cage limbs 82 of the respective implant assembly 78 to removably mount the stretcher on the assembly. The posterior capsule stretcher 76b is separable from the cage 80 of its respective implant assembly 78, as is the lens 84 of the assembly, for insertion of these parts into the eye separately and reassembly of the parts within the eye by the surgeon. The capsule stretcher 76b may be constructed of a foldable inert optically transparent material, such as silicone, to permit the stretcher, like the cage, to be folded to a compact configuration for insertion through a small incision, or it may be a hard optically transparent material, such as methyl methacrylate. The haptics 88c of the posterior capsule stretcher 76c are somewhat longer than those of the stretcher 76b and contain slots 92c which receive the rear arcuate extremities of the cage limbs 82 of the respective implant assembly 78 to permanently mount the stretcher on the assembly. The capsule stretcher 76c may be constructed of a foldable inert optically transparent material, such as silicone, to permit the stretcher and its supporting cage 80 to be folded as a unit to a compact configuration for insertion through a small incision, or it may be a hard optically transparent material, such as methyl methacrylate.

The curvature of the posterior surfaces 94b, 94c of the capsule stretcher optical portions 86b, 86c may be substantially the same as, more convex than, or less convex than the natural curvature of the posterior capsule 32 of the human capsular bag 28. Preferably, the curvature of the stretcher posterior surface is more convex than the natural curvature of the posterior capsule; that is to say, the capsule stretcher posterior surface has a radius of curvature which is smaller than the natural radius of curvature of the posterior capsule 32. As a consequence, when the intraocular implants 76b, 76c are implanted in the eye, their posterior stretcher surfaces 94b, 94c indent the posterior capsule 32 in such a way that during the healing process of fibrosis which occurs after surgery, the capsular bag 28 is effectively "shrink-wrapped" about the implant. The posterior capsule, which is very elastic, is thereby drawn tightly against and stretched tightly across the posterior stretcher surfaces 94b, 94c in such a way as to form a seal between the stretcher surface and the posterior capsule. This seal greatly reduces opacification of the posterior capsule which is a major complication of modern cataract surgery and has been reported to occur in as many as 60% of cases.

The posterior capsule stretchers 76b, 76c provide other benefits as well. One of these additional benefits resides in the fact that the seal formed by tight opposition of the human posterior capsule 32 to the posterior capsule stretchers permits the surgeon to make a central opening in the posterior capsule 32 with a Y.A.G laser or other means in the event the posterior capsule becomes cloudy and obscures vision without postoperative vitreous leakage into the capsular bag 28. In the absence of such a seal, vitreous, which is a viscous gel, would leak from the vitreous cavity 22 into the capsular bag 28. Thus, the posterior capsule stretchers aid in preventing postoperative increase of the vitreous volume of the eye by pushing the posterior capsule posteriorly to its preoperative position and by preventing vitreous from expanding into the bag should a posterior capsulotomy be necessary because of clouding of the posterior capsule. This greatly decreases or prevents two complications of cataract surgery, namely cystoid macular edema and retinal detachment.

The optical portions 86b, 86c of the posterior capsule stretchers 76b, 76c may perform only the posterior capsule stretching and sealing functions discussed above without refracting the light passing through these optical portions. Alternatively, the capsule stretcher optical portions may be lens-shaped to form intraocular lens systems 96b, 96c with the lenses 84 of the respective intraocular implants 50b, 50c. The lenses 84 are the primary lenses of these lens systems. The stretcher optical portions or lenses 86b, 86c have anterior surfaces 98b, 98c which can have various contours depending upon the desired optical characteristics of the overall lens system 96. Thus, the anterior surface 98 can be plano (FIGS. 12 and 13) to provide the stretcher optical portions with a plus power, a Fresnel surface (FIG. 14) to provide the optical portions with either a plus or minus power, or concave (FIGS. 15 and 16) to provide the optical portions with a minus power. Shaping the anterior surfaces of the stretcher optical portions to provide the optical portions with a minus power allows the primary lens 84 of each implant 50b, 50c to have more plus power than 30 would otherwise be needed to focus the eye. This increases the change in power of the lens system achieved by any given adjustment of the primary lens 84, and, conversely, permits the power of the primary lens to be increased and the primary lens adjustment necessary to achieve a given change in focus distance to be reduced.

FIGS. 17–43 illustrate accommodating intraocular implants according to the invention which are adjustable by some action of the wearer to a near focus position for reading or other close viewing and to a distant focus position for distant viewing. One of the implants also embodies a time release ophthalmic drug dispensing system, and another of the implants comprises a telescopic magnifying system which enables a person with macular degeneration to see.

The accommodating implant 50d illustrated in FIGS. 17–20 comprises a lens holder or cage 100, an accommodating lens assembly 102, and means 104 mounting the lens assembly on the cage. The cage 100 and mounting means 104 illustrated are essentially identical to those of FIGS. 2–5 and thus need not be described in detail. Suffice it to say that the cage 100 has a base ring 106 and arcuate posterior limbs 108. The mounting means 104 comprises a screw 110 on the lens assembly 102 threaded into a nut 112 rotatable in the cage base ring 106 for axial adjustment of the screw relative to the cage by rotation of the nut in the same manner as explained earlier in connection with FIGS. 2–5. It will be evident that accommodating implants according to the invention may utilize a lens assembly mounting means similar to that of FIG. 8.

Figure 17:
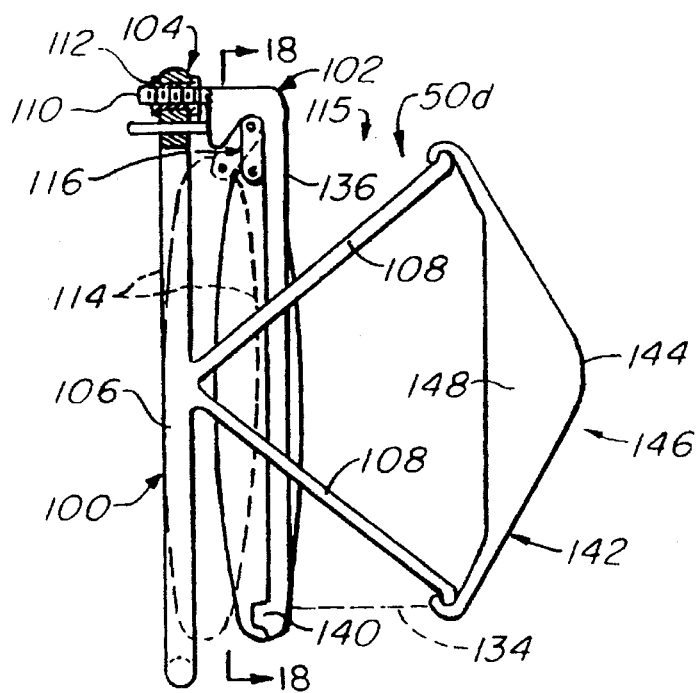
FIG. 17 is an enlarged section through an accommodating intraocular implant according to the invention.
Figure 19:
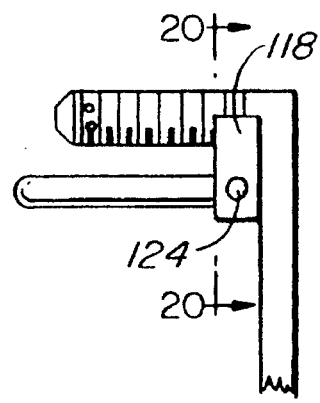
FIG. 19 is a side elevation of one component of the lens assembly in FIG. 18.

The accommodating lens assembly 102 comprises a lens 114 proper and means 115 supporting the lens on the mounting screw 110 for (a) adjustment of the lens by the surgeon during surgery to focus the lens on the retina of the eye and (b) accommodating adjustment or movement of the lens between a distant focus position, shown in full lines in FIG. 17, and a near focus position, shown in broken lines in FIG. 17, by some postoperative action of the patient, in this case by tilting movement of his head. Lens supporting means 115 comprises a swing mechanism 116 including a bracket 118 rigid on and disposed in a transverse plane of the screw adjacent its posterior end. This bracket extends below and laterally to opposite sides of the screw in a transverse plane of the screw. A hinge plate 120 has a first pair of coaxial journals 122 which straddle the bracket in the plane of the bracket and engage rotatably within coaxial sockets 124 in the bracket. These journals and sockets pivotally mount the hinge plate on the bracket for rotation of the hinge plate on a pivot axis 126 located in the plane of the bracket and extending transverse to the screw 110. The hinge plate 120 has a second pair of coaxial journals 128 which straddle a superior portion of the lens 114 in the plane of the lens and engage rotatably within coaxial sockets 130 in the lens to pivotally connect the hinge plate to the lens on a pivot axis 132. Pivot axis 132 parallels and is spaced laterally from the pivot axis 126 and is disposed in the plane of the lens.

As will be explained in more detail presently, the accommodating intraocular implant 50d is implanted in the eye in essentially the same way as the earlier described implants. In the implanted position of the implant, its lens system mounting screw 110 is uppermost, substantially parallel to the optic axis of the eye, and substantially horizontal when the implantee is standing erect with his head upright. The screw is substantially vertical when the implantee is lying on his back in a horizontal position. The swing mechanism pivot axes 126, 132 are substantially horizontal in both of these positions as well as when the implantee inclines his head up or down. Accordingly, gravity constantly urges the lens 114 and hinge plate 120 toward a vertical hanging position. If the lens and the hinge plate were not restrained in any way, they would normally hang in a common vertical plane transverse to the axis of the mounting screw 110 and to the optic axis of the eye, as shown in solid lines in FIG. 17, when the implantee's head is upright.

As explained more fully below, the accommodating implant lens 114 is adjustable during surgery to focus the lens on the retina of the patient's eye. The lens is adjustable postoperatively to its broken line near focus or near vision position in FIG. 17 by downward tilting of the implantee's head to a reading position and to its full line distant focus or distant vision position of FIG. 17 by upward tilting of the head. When the implantee's head is tilted downwardly, gravity urges the lens 114 and hinge plate 120 anteriorly relative to the cage 100 and the eye. If not restrained in any way, the lens and hinge plate would then hang in a common vertical plane inclined at an acute angle to the axis of the eye in such a way the plane of the lens would incline anteriorly of the eye from the superior edge to the inferior edge of the lens. Similarly, if the implantee tilts his head upwardly or lies down, gravity urges the lens and hinge plate posteriorly in the eye. If not restrained in any way, the lens and hinge plate would then hang in a common vertical plane inclined at an acute angle relative to the axis of the eye in such a way that the plane of the lens would incline posteriorly of the eye from the superior edge to the inferior edge of the lens.

Proper optical functioning of the implant 50d, however, requires that the plane of the lens remain substantially normal to the axis of the mounting screw 110 and to the optic axis of the eye throughout the range of the focussing adjustment of the lens and in both the near focus and distant focus positions of the lens. The lens supporting means 115 maintains this proper lens orientation relative to the eye.

In this regard, it will be seen that the hinge plate 120 pivotally supports the superior portion of the lens on the bracket 118 for limited (arcuate) anterior and posterior movement of this superior lens portion relative to the cage 100 and hence relative to the eye. In this regard, the distance $d_1$ in FIG. 18A between the hinge axis 126 and the superior edge of the lens 114 and the distance $d_2$ between this edge and the hinge axis 132 are calculated to provide a predetermined anterior movement of the superior edge of the lens from a plane normal to the screw 110 containing the hinge axis 126 which would provide the implant an adequate increase in plus power to enable the implantee to see near objects clearly. The amount of this movement would also be dependent upon the power of the implant lens 114.

The lens supporting means 115 further comprises anterior lens positioning means 134 for limiting anterior movement of the inferior portion of the lens and posterior lens positioning means 136 for limiting posterior movement of both the superior and inferior portions of the lens, that is, limiting posterior movement of the entire lens. The hinge plate 120 and anterior positioning means 134 cooperate to limit anterior movement of the lens 114 and to position the lens in its broken line near focus position of FIG. 17 when the implantee tilts his head down. The posterior lens positioning means 136 limits posterior movement of the lens to and positions the lens in its solid line distant focus position of FIG. 17 when the implantee tilts his head up or lies down and aids in retaining the lens in this position when the implantee's head is upright. In both of these lens positions, the plane of the lens is substantially normal to the axis of screw 110 and hence normal to the axis of the eye.

The illustrated anterior lens positioning means 134 comprises a thread or the like connected between the inferior edge of the lens 114 and the lower posterior limb 108 of the cage 100 to limit anterior movement of the inferior lens portion to its broken line position of FIG. 17. The posterior lens positioning means 136 comprises a pair of arcuate arms 138 rigidly joined at one end to opposite sides of the mounting screw 110, immediately behind the bracket 118. These arms extend laterally from the screw in a common plane transverse to the screw and parallel to the pivot axes 126, 132 of the swing mechanism 116. The arms bow outwardly away from one another and then inwardly toward one another in their common plane in the direction of their inferior ends 139*a*. As shown best in FIG. 18, the superior portions 139*b* of the arms 138 adjacent the mounting screw 110 are disposed to engage and limit posterior pivotal movement of the hinge plate 118 and thereby also the superior portion of the lens 114 to the solid line positions of FIG. 17. The inferior ends 139*a* of the arms turn inwardly to underlie flanges 140 at opposite sides of the inferior portion of the lens 114 and limit posterior movement of the inferior lens portion to the solid line position of FIG. 17. Between the arm ends 139*a* and arm portions 139*b*, the arms 138 bow outwardly to lie outside the optical portion of the lens 114, as shown. The arm portions 139*a*, 139*b* of the lens supporting means 138 thus cooperate to limit posterior movement of the lens 114 to its solid line distant focus position of FIG. 17.

Various types of lenses may be utilized in the accommodating intraocular implant 50*d*. For example, lens 114 may be biconvex (FIG. 21*a*), plano-convex (FIG. 21*b*), plano-convex with a planar Fresnel surface (FIG. 21*c*), planar with one Fresnel surface (FIG. 21*d*), or planar with two Fresnel surfaces (FIG. 21*e*), or may be concave-convex (FIG. 21*f*) and may be single vision or multifocal.

The illustrated accommodating intraocular implant 50*d* includes a posterior capsule stretcher 142 mounted on the posterior limbs 108 of the implant cage 100. This capsule stretcher is identical in construction and purpose to that illustrated in FIGS. 9, 11, and 12 although it may be like that illustrated in FIG. 13. Accordingly, it is unnecessary to describe either the capsule stretcher 142 or its functions and advantages in detail. Suffice it to say that the implant lens 114 and the optical portion 144 of the posterior capsule stretcher 142 together form a lens system 146 in which the lens 114 is an accommodating primary lens. As discussed earlier in connection with FIGS. 9–13, the anterior surface 148 of the optical portion 144 can have various shapes depending upon the desired optical characteristics of the overall lens system 146. Thus, the anterior surface 148 can be plano (FIGS. 12 and 13) to provide the optical portion 86 with a plus power, a Fresnel surface (FIG. 14) to provide the optical portion with either a plus or minus power, or concave (FIGS. 15 and 16) to provide the optical portion with a minus power. Shaping the anterior surface to provide the optical portion 86 with a minimum power allows the primary lens 114 of the implant 50*d* to have more plus power than would otherwise be needed to focus the eye. This is particularly beneficial in the accommodating intraocular implant 50*d* because a capsule stretcher having an optical portion 144 of minimum power permits the use of an accommodating primary lens 114 with greater power. Increasing the power of the primary lens, in turn, reduces the movement or displacement of this lens necessary to provide effective vision accommodation, i.e. the accommodating lens movement between its solid and broken lines in FIG. 17.

The accommodating lens assembly 102 is separable from the implant cage 100 by disengaging the lens assembly mounting screw 110 from the cage nut 112. The posterior capsule stretcher 142 is separable from the cage. This permits the cage, capsule stretcher, and lens assembly to be inserted into the eye separately and reassembled by the surgeon within the eye. Moreover, the materials of the lens 114 and/or the hinge plate 118 may be sufficiently flexible to permit their separation from one another and from the mounting bracket 118 for insertion into the eye separately and reassembly within the eye by the surgeon. At least some of the separable parts of the implant may be constructed of the foldable intraocular implant materials mentioned earlier to permit these parts to be folded to a compact configuration for insertion into the eye through a small incision.

It is evident from the foregoing description that the accommodating intraocular implant 50*d* is implantable in a patient's eye in the same manner as the earlier described implants. Assuming that the patient is lying horizontally on his back, the posterior lens positioning means 136 of the implant supports the lens 114 in its solid line distant focus position of FIG. 17 relative to the cage 100 and patient's eye with the lens disposed in generally horizontal plane normal to the optic axis of the eye. The surgeon may thus accurately focus the lens system 146 on the retina 24 of the patient's eye by rotating the cage nut 112 to adjust the accommodating lens assembly 102 as a unit, and thereby the lens 114, toward and away from the retina in much the same manner as explained earlier in connection with FIGS. 2–8. Postoperative adjustment of the lens between its distant focus or distant vision position and its near focus or near vision position is accomplished by up and down tilting movement of the implantee's head. Thus, when his head occupies its normally upright position (FIG. 22*a*), the lens 114 is retained by gravity in its illustrated distant focus position relative to the eye, which is the solid line position in FIG. 17 corresponding to the solid line lens position in FIG. 17, to provide the implantee with distant vision. The lens will remain in this position relative the eye if the implantee tilts his head upwardly. If he lowers his head to reading position (FIG. 22*b*), the lens 114 is moved by gravity to its illustrated near focus position, which is the broken line position in FIG. 17 corresponding to the broken line lens position in FIG. 17, to provide him with near vision. The lens is returned to its distant focus position when the implantee again raises his head. The lens 114 mount weights 141 for aiding this accommodating lens movement. These weights may be magnetic to permit movement of the lens between its distant and near focus postions by external magnets which may be mounted in rings worn by the implantee.

FIGS. 23–31 illustrate modified accommodating intraocular implants according to the invention which are essentially identical to the accommodating implant 50d of FIGS. 17–22 except for the anterior and positioning means for limiting anterior and posterior movement of the movable accommodating lens to its near focus and distant focus positions. For this reason, only the portions of the modified implants which differ from those of the implant 50d are illustrated in FIGS. 23–30 and will be described. Nevertheless, for the sake of convenience, even though FIGS. 23–31 illustrate only portions of the complete implants, the implant portions which are shown are referred as implants and designated by the reference numeral 50 with an appropriate suffix. Moreover, those illustrated parts of the modified implants which correspond to parts of the implant 50d are identified by the same reference numerals, with an appropriate suffix, as their corresponding parts of the implant 50d.

The implant 50e of FIGS. 23 and 24 includes lens positioning means 136e for limiting both anterior and posterior movement of the inferior portion of the accommodating implant lens 11ee. This lens positioning means is identical to the posterior lens positioning means 136 in FIGS. 17–22 except that the inferior end 139e of each arm 138e (only one arm shown) of the lens positioning means extends anteriorly through an opening 150e in the adjacent flange 140e of the accommodating lens 114e and has a button 152e at its anterior end. Implant 50e is otherwise identical to and is implanted, focussed, and used in essentially the same way as that of FIGS. 17–22, except that the inferior arm ends 119e cooperate with the implant hinge plate (not shown in FIGS. 23 and 24) to limit both posterior and anterior movement of the lens 114e to its distant focus position and near focus position corresponding to the accommodating lens position illustrated in solid and broken lines in FIG. 17.

The implant 50f of FIGS. 25 and 26 includes lens positioning means 136f which also cooperates with the implant hinge plate (not shown in FIGS. 25 and 26) to limit both anterior and posterior movement of the accommodating implant lens 114f. This lens positioning means, like that in FIGS. 23 and 24, is identical to the lens positioning means 136 in FIGS. 17–22 except that the inferior end 139f of each arm 138f (only one arm shown) of the lens positioning means 136f extends inwardly in the plane of the arms and into an anteriorly and posteriorly elongated guideway 154f within a guide 156f rigidly joined to the adjacent inferior edge of the lens. On the inner end of each arm end 139f is a button 158f which retains the end in the guideway. Implant 50f is otherwise identical to and is implanted, focussed and used in essentially the same way as the implant of FIGS. 17–22. The arm ends 139f and guides 156f cooperate with the implant hinge plate to limit both anterior and posterior movement of the lens to its distant and near focus positions corresponding to the solid and broken line lens positions in FIG. 17.

The modified accommodating implant 50 g of FIGS. 27–29 omits the posterior lens positioning means 136 of the implant 50d and includes, instead, a pair of lugs 160g along the inferior edge of the lens mounting bracket 118g. These lugs are disposed to straddle a lug 162g along the superior edge of the accommodating lens 114g when the lens and hinge plate 120g occupy their illustrated positions in a common plane normal to the axis of the lens assembly mounting screw 110g. This position is the distant focus position of the lens corresponding to the solid line lens position in FIG. 17 and is the lens position used for focusing the implant lens system on the retina of the patient's eye. The lugs 160g and 162g contain bores which are coaxially aligned in this lens position to slidably receive a removable pin 164g which locks the lens in position. Anterior movement of the inferior portion of the lens 114g is limited by engagement of a depending lip 166g along the inferior edge of the lens with an upstanding stop 168g along the inferior portion of the cage base ring 106g. Implant 50g is otherwise identical to and is implanted, focussed, and used in essentially the same way as the implant 50d of FIGS. 17–22. The lens lip 166g and cage stop 168g cooperate with the implant hinge plate to limit anterior movement of the lens to its near focus position corresponding to the broken line lens positions in FIG. 17. The lens hangs vertically in its distant focus position when the implantee's head is upright. During surgery, the lens 114g is locked in its focusing position normal to the axis of the mounting screw 110g and axis of the eye by the pin 164g which is removed at the conclusion of surgery to free the lens for anterior and posterior vision accommodating movement.

The modified implant 50h of FIGS. 30 and 31, like that of FIGS. 27–29, omits the posterior lens postioning means 136 of the implant 50d. Posterior movement of the superior portion of the lens 114h is limited by abutment of an upstanding stop 170h on the implant hinge plate 120h with the posterior end of the implant lens assembly mounting screw 110h. The hinge plate limits anterior movement of the superior lens portion in the same manner as described in connection with FIG. 17. Anterior and posterior movement of the inferior portion of the lens is limited by contact of a lip 172h depending from the inferior edge of the lens with upstanding anterior and posterior limit stops 174h, 176h on the inferior portion of the cage base ring 106h. Implant 50h is otherwise identical to and is implanted, focussed and used in essentially the same way as the implant of FIGS. 17–22. The hinge plate 120h, hinge plate stop 170h, lens lip 172h, and cage stops 172h, 174h cooperate to limit both anterior and posterior movement of the lens to its distant and near focus positions corresponding to the solid and broken line lens positions in FIG. 17.

FIGS. 32–38 illustrate modified accommodating intraocular implants according to the invention in which the accommodating lens is slidably supported on the implant lens holder or cage for movement between its near focus and distant focus postions. In the implant 50i of FIGS. 32–34, the cage 100i has two substantially parallel slides 178i extending between and joined to the cage base ring 106i and the upper cage limb 108i. A posterior capsule stretcher 144i is attached to the limbs. The accommodating lens 114i has flanges 180i at opposite sides of its superior portion containing bores 182i through which the cage slides past to slidably support the lens for anterior and posterior movement relative to the cage 100i between its solid line distant focus position of FIG. 32 at the posterior ends of the slides and its broken line near focus position of FIG. 32 at anterior ends of the slides. These positions correspond to the solid and broken line lens positions in FIG. 17. As shown best in FIG. 32, the slides 178i slope downwardly at a small angle relative to the cage in their posterior direction. The angle of this slope relative to the cage 100i is such that when the axis of the cage is horizontal, as shown in FIG. 32 and as it is when the implantee's head is upright, the slides 178i slope downwardly relative to the horizontal in their posterior direction, and the lens slides posteriorly to its solid line distant focus position. When the implantee tilts his head down, the slides slope downwardly relative to the horizontal in their anterior direction, and the lens slides anteriorly to its broken line near focus position. The axes of the flange bores 182*i* are inclined relative to the plane of the lens at an angle such that the plane of the lens remains normal to the axis of the cage 100*i*. The lens 114*i* may mount weights 184*i* for aiding sliding movement of the lens between its near and distant focus positions. These weights may be magnetic to permit movement of the lens between these positions by external magnets, such as small magnets mounted in rings to be worn by the implantee.

The accommodating implant 50*j* of FIGS. 35–38 is similar to the implant 50*i* just described except in the following respects. The accommodating lens 114*j* of implant 50*j* has diametrically opposite flanges 180*j* slidably supported on slides 178*j* for sliding movement of the lens between its solid line distant focus position and its broken line near focus position of FIG. 35. In this case, the slides are located approximately midway between the cage limbs 108*j* and are secured at their posterior ends to the posterior capsule stretcher 144*j* of the implant. The slides 178*j* slope downwardly toward their posterior ends like the slides 178*i* so that the lens is movable to its near and distant focus positions by up and down tilting movement of the implantee's head in the manner explained above. Movement of the lens between these positions in response to tilting movement of the implantee's head is aided by weights 184*j*, such as balls, movably contained within tubes 186*j* extending through the lens flanges 180*j* normal to the plane of the lens and fixed to the flanges. These weights, like those in the implant 50*i*, may be magnetic to permit movement of the lens between its near focus and distant focus positions by external magnets.

As mentioned earlier, one important feature of the invention resides in providing an intraocular implant according to the invention with a time release ophthalmic drug release or dispensing means for introducing a selected ophthalmic drug into the eye at a controlled rate over an extended period of time. The intraocular implant 50*j* of FIGS. 35–38 embodies such a drug release or dispensing means 188*j*. This drug dispensing means comprises a time release capsule 190*j* fixed within a hole 192*j* in the ring of the implant cage 100*j*. This time release capsule contains the drug to be dispensed in such a way that the drug is slowly introduced into the eye at a relatively controlled rate over an extended period of time and may be replenished periodically. For example, the time release drug capsule may be one which is substantially totally consumed over a period of time, as by dissolution into the fluid within the eye, in which case periodic replenishment of the drug is accomplished by periodically placing a fresh drug capsule into the implant hole. 192*j*. Alternatively, the time release capsule may comprise a non-consumable porous capsule which contains the drug and gradually releases it into the eye and which permits periodic replenishment of the drug in the capsule by either removing, refilling, and replacing the capsule or injecting more drug into the capsule while it remains within the eye and mounted on the implant. While the drug dispensing means 188*j* is shown as being embodied in the intraocular implant configuration of FIGS. 35–38, it is evident that the dispensing means may be embodied in any of the disclosed intraocular implants of the invention.

Figure 39:
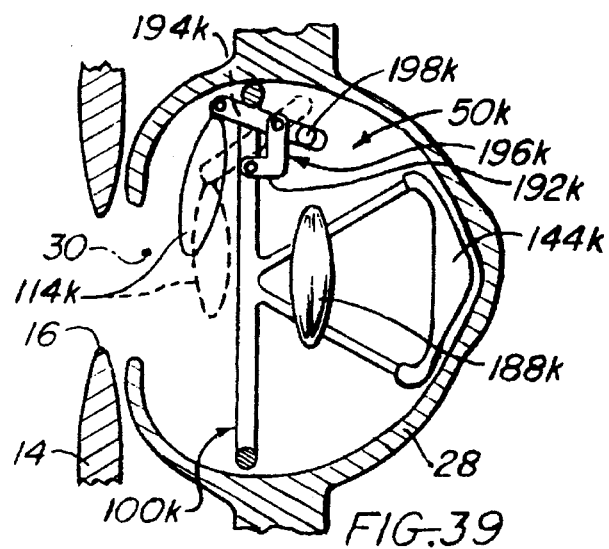
FIG. 39 diagrammatically illustrates a further modified intraocular implant according to the invention implanted within the capsular bag of human eye.

The modified accommodating intraocular implant 50*k* illustrated in diagrammatic fashion in FIG. 39 is shown within a human capsular bag 28 having a circular anterior capsulotomy 30. The implant comprises a lens holder or cage 100*k*, a relatively fixed lens 188*k* and a posterior capsule stretcher 144*k* relatively fixedly mounted on the cage, an accommodating lens 114*k*, and means 192*k* mounting the accommodating lens on the cage for movement between its solid line distant focus position and its broken line near focus position. In its distant focus position, the accommodating lens is retracted out of the path of light rays entering the eye. In its near focus position, the accommodating lens is optically aligned with the lens 188*k* and the posterior capsule stretcher 144*k*. The lens mounting means 192*k* comprises a beam 194*k* and a fulcrum means 196*k* which pivotally supports the beam between its ends for limited rotation between its solid and broken lines. The accommodating lens 114*k* is pivotally attached to the anterior end of the beam in such a way that rotation of the beam to its full line position elevates the accommodating lens to its full line distant focus position. Rotation of the beam to its broken line position lowers the accommodating lens to its broken line near focus position. Movable endwise within the beam is a weight 198*k*, such as a ball. The implant 50*k* is arranged in such a way that downward tilting of the implantee's head causes the weight 198*k* to move to the anterior end of the beam 194*k* and rotate the beam to its broken line position and thereby lower the accommodating lens 190*k* to its near focus position. Upward tilting of the head to a position in which the beam slopes downwardly toward its posterior end causes movement of the weight to the posterior end of the beam to rotate the beam to its solid line position and thereby elevate the lens to its distant focus position. The entire lens assembly comprising the accommodating lens 114*k*, its beam support, and the fixed lens 188*k* may be mounted on the cage 100*k* for focusing adjustment relative to the cage in the same manner as the other accommodating implants of the invention.

Figure 40:
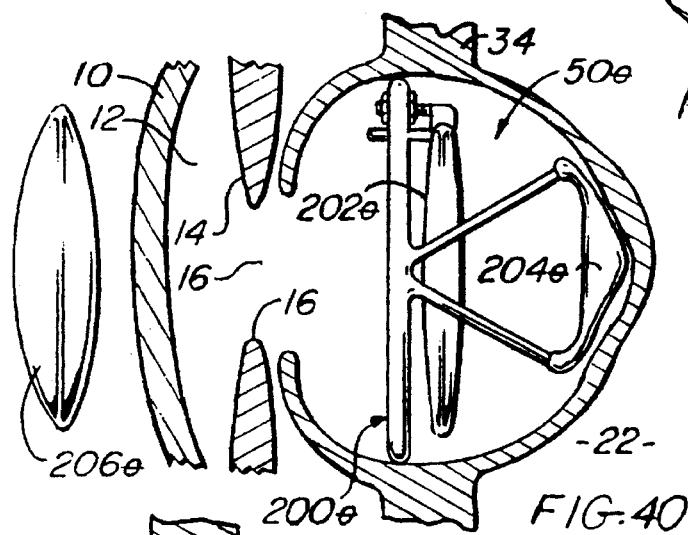
FIG. 40 illustrates an intraocular telescopic magnifying system according to the invention for magnifying images on the retina of a person with macular degeneration.

FIG. 40 illustrates a telescopic magnifying optical system 50*o* according to the invention for magnifying images on the retina. This magnifying optical system is particularly beneficial for a person with macular degeneration because it permits the person to see. The magnifying system comprises two intraocular lenses within the eye and, if necessary or desirable, a third lens. In the particular embodiment illustrated, the two intraocular lenses are provided by an intraocular implant 50*o* positioned within the capsular bag 28 of the eye. This implant is identical to that of FIGS. 17–20 and hence need not be described except to say that the implant has a cage 200*o* mounting a swinging accommodating lens 202*o* and a posterior capsule stretcher including an optical portion or lens 204*o*. These two lenses 202*o* and 204*o* can be optically designed to function as an intraocular telescopic magnifying system for the purpose stated above. In some cases, it may be desirable or necessary to provide the telescopic magnifying system with a third lens 206*o*. In FIG. 40, this third lens is an external lens to be mounted in an eyeglass or spectacle frame (not shown) worn by implantee. Alternatively, the third lens may be a contact lens or an intraocular lens implanted in the anterior chamber of the eye. The accommodating lens 202*o* is movable anteriorly and posteriorly in the manner explained earlier to focus the magnifying lens system at different distances.

Figure 42:
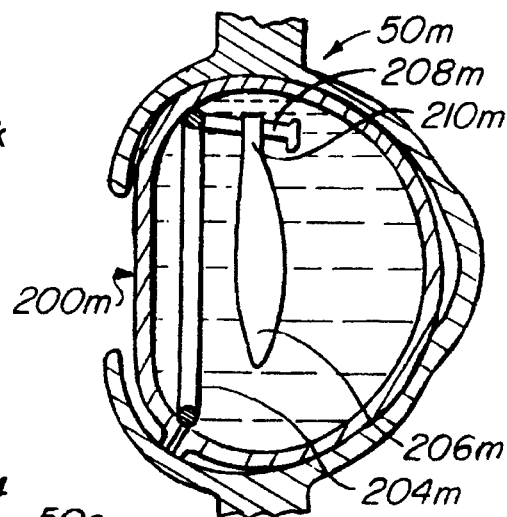
FIG. 42 illustrates a modified intraocular balloon implant according to the invention implanted within the capsular bag of human eye.
Figure 41A:
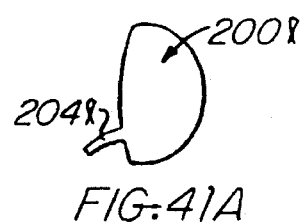
FIG. 41A is a perspective view on reduced scale of the balloon implant in FIG. 40.
Figure 41:
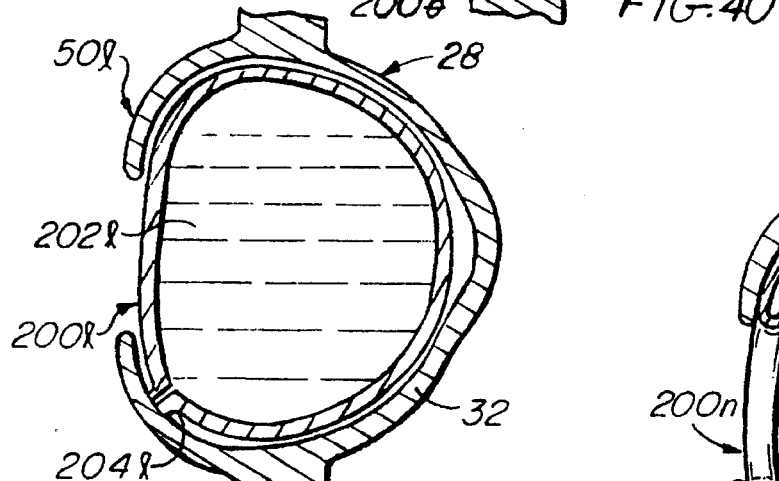
FIG. 41 illustrates an intraocular balloon implant according to the invention implanted within the capsular bag of human eye.
Figure 43:
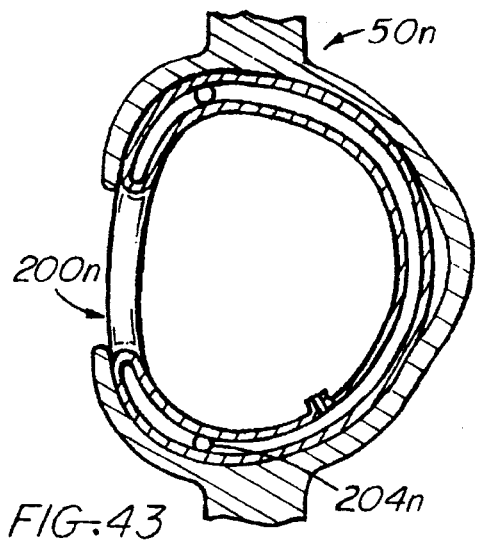
FIG. 43 illustrates a further modified intraocular balloon implant according to the invention implanted within the capsular bag of human eye.

FIGS. 41–43 illustrate inflatable balloon-type accommodating intraocular implants according to the invention for replacing a natural nucleus and cortex which have been surgically removed from the capsular bag 28 of a human eye. The balloon implant 50*l* of FIG. 41 comprises an inflatable, optically clear balloon 200*l* which is placed within the capsular bag and inflated or filled with an inert optically clear material 202*l*, such as silicone, through an inlet 204*l*. The balloon is shaped so that when thus inflated, it presses outwardly against the bag to prevent wrinkling of its posterior capsule 32 and anterior capsule rim about and retain the bag in a shape which conforms closely to its natural shape. The balloon 200*l*, silicone 202*l*, and the capsular bag 28 form an artificial intraocular lens having a shape and optical characteristics conforming closely to those of the human lens. This artificial lens can be focussed on the retina for distant vision by the surgeon during surgery by refracting the patient and changing the volume and refractive index of the silicone. After recovery from surgery, the patient should be able to focus the lens for near vision by contracting the ciliary muscles of the eye in the usual physiological manner. Another advantage of the balloon resides in the fact that it blocks migration of epithelial cells to the posterior capsule of the bag, thus inhibiting or preventing opacification of this capsule.

The modified balloon implant 50*m* of FIG. 42 includes a silicone filled balloon 200*m* similar to the balloon 200*l* except that balloon 200*m* has a stabilizing ring 204*m* joined to the anterior wall of the balloon for retaining the balloon within the capsular bag 28. The balloon performs the same function as the balloon in FIG. 40. In addition to its purpose of retaining the balloon 200*m* within the capsular bag 28, the retaining ring supports an accommodating lens 206*m* within the balloon. To this end, the ring includes a stem 208*m* which extends posteriorly from the ring, and the lens 206*m* has a bracket 210*m* which slides on and is retained against rotation about the stem 208*m*. Stem 208*m* slopes downwardly at a small angle relative in the same manner as the slides 178*i* and 178*j* in FIGS. 32 and 35 so that the lens slides rearwardly when the implantee's head is upright and forwardly when the implantee tilts his head downwardly. The lens formed by the balloon 200*m* and its contained silicone and the lens 206*m* within the balloon can be optically designed to form an accommodating lens system. It is evident, of course, that the lens 206*m* may be replaced by any of the earlier described intraocular implants of the invention. FIG. 43 illustrates a balloon implant 50*n* comprising a double-walled silicone filled balloon 200*n* containing a stabilizing ring 204*n*.

It will be evident at this point that the intraocular implants of the invention are implanted in a patient's eye in a position wherein an axis of the lens holder of the implant extends in the anterior and posterior directions of the eye and the holder has anterior and posterior sides relative to the eye. In FIGS. 40–42, this is the axis of the balloon passing through the centers of the anterior and posterior sides of the balloon. In the other figures, the anterior-posterior axis of the lens holder is the central axis of the base ring of the holder cage. Except for the is embodiment of FIG. 39, the adjustable focussing lens adjustable along this axis by the surgeon during surgery to focus the implant on the retina of the eye and is postoperatively adjustable along the axis to vary the focus between near and distant object distances by movement of the implantee's head and/or magnetic action. The lens systems of the implants comprising the two lenses in FIG. 39 and the lens and posterior capsule stretcher in other figures, may be optically designed to provide telescopic vision by themselves or in conjunction with external lenses worn by the implantee. The curvature of the posterior surface of the posterior capsule stretcher and the posterior wall of the balloon may be substantially the same, greater than, or less than the natural curvature of the posterior capsule of the capsular bag of the eye. A greater curvature is preferable, however, since it achieves tighter stretching of the posterior capsule across the capsule stretcher of posterior balloon wall, as the case may be, and thereby more effective prevention of opacification of the posterior capsule.

The optical elements of the present intraocular implants may be fabricated from any suitable optical materials. If desired, one or more of these elements may be optically conditioned to block certain wavelengths of light, such as ultraviolet wavelengths, and pass other wavelengths. While the disclosed implants are mounted within the human capsular bag 28, it is evident that at least some of the implants may be mounted in any of the eye chambers or cavity.

I claim:

1. The method of surgically implanting an intraocular lens in a patient's eye through an incision in the eye, comprising the steps of:

inserting said lens and a lens holder into the eye, implanting said lens holder in the eye, and adjusting said lens bodily relative to the implanted holder along the axis of the eye to focus said lens on the retina of the eye without changing either the shape of the lens or the position of the lens about said axis.

2. The method of claim 1, wherein:

said implant comprises threaded means connecting said holder and lens including a member which is rotatable to adjust said lens relative to said holder, and said step of adjusting said lens relative to said holder comprises rotating said rotatable member.

3. The method of implanting an intraocular lens in a patient's eye through an incision in the eye, comprising the steps of:

providing a foldable resilient lens holder which has a normal unfolded configuration and is foldable to a compact folded configuration wherein the holder stores elastic strain energy sufficient to unfold the holder from said compact folded configuration to said normal unfolded configuration, inserting said lens holder into the eye through said incision while the holder is in said compact folded configuration, and then implanting the holder in a fixed implanted position in the eye by releasing the folded holder within the eye to effect unfolding of the holder within the eye by said elastic strain energy from said compact folded configuration to said normal unfolded configuration with the holder disposed in said fixed implanted position in the eye, inserting said lens into the eye through said incision, and mounting said lens on the unfolded implanted holder while the holder is in said implanted position.

4. The method of claim 3 wherein:

said holder in said normal unfolded configuration and implanted position has normally anterior and posterior sides relative to the eye forming a space between said sides which is sized to receive said lens in a portion of said space wherein the lens is adjustable relative to the holder in the anterior/posterior direction of the holder without projection of the lens beyond said sides in said anterior/posterior direction, and light rays entering the eye can pass through the holder in anterior/posterior direction, and said step of mounting said lens on said holder comprises mounting the lens on the holder with the lens positioned in said portion of said space between said holder sides.

5. The method of restoring vision to and maintaining the vitreous volume of a patient's eye containing a capsular bag from which the nucleus and cortex have been removed in such a way as to leave the posterior capsule of the bag intact, comprising the steps of:

providing an optical implant including a lens and a resilient foldable lens holder, the lens holder having normally anterior and posterior sides, posterior capsule engaging means at said posterior side, and a normal unfolded configuration in which said anterior and posterior sides of the holder form a space within said holder between said sides and light rays can pass through said holder from said anterior side to said posterior side of the holder, and wherein said holder is foldable to a compact folded configuration in which the holder stores elastic strain energy sufficient to unfold the holder from said compact folded configuration to said normal unfolded configuration, implanting said holder in the eye by inserting the holder into said capsular bag through an incision in the eye while the holder is in its compact folded configuration and releasing the folded holder within said capsular bag to effect unfolding of the holder within the bag by said stored elastic strain energy from said compact folded configuration to said normal unfolded configuration with the holder disposed in a fixed implanted position within said bag wherein said holder is disposed between said posterior capsule and said anterior rim of the bag and said posterior capsule engaging means presses against said posterior capsule to retain said posterior capsule substantially in its natural shape, inserting said lens into said capsular bag through said incision, and while said holder is in said implanted position, mounting the lens on the unfolded implanted holder with the lens located within said space in the unfolded holder.

6. The method of claim 5, wherein:

said lens holder is a cage having an anterior ring and arcuate posterior limbs joined to and extend rearwardly from said ring, said space has an anterior portion immediately behind said ring, and said step of mounting said lens on the unfolded holder comprises mounting said lens on said cage with the lens located within said anterior portion of said space.

7. The method of implanting an intraocular lens in a patient's eye containing a capsular bag from which the natural lens matrix has been removed and which bag includes a posterior capsule and an anterior capsulotomy circumferentially surrounded by an anterior capsular remnant, comprising the steps of:

inserting a lens holder into said capsular bag through an incision in the eye and said anterior capsulotomy, implanting said lens holder in said bag in a fixed implanted position within the bag wherein the holder is located between said posterior capsule and said anterior remnant, inserting said lens into said bag through said incision and said anterior capsulotomy, mounting said lens on the implanted holder while the holder is in said implanted position, and adjusting said lens bodily relative to the implanted holder along the axis of the eye to focus said lens on the retina of the eye without changing either the shape of the lens or the position of the lens about said axis.

8. The method of claim 7 wherein:

said holder in said implanted position has normally anterior and posterior sides engaging said anterior remnant and said posterior capsule, respectively, and a space between said sides, and light rays entering the eye can pass through the holder in a direction from said anterior side to said posterior side, and said step of mounting said lens on said holder comprises mounting the lens on the holder within said space and between said holder sides.

9. The method of implanting an intraocular lens in a patient's eye containing a capsular bag from which the natural lens matrix has been removed and which bag includes a posterior capsule and an anterior capsulotomy circumferentially surrounded by an anterior capsular remnant, comprising the steps of:

providing a foldable resilient lens holder which has a normal unfolded configuration and is foldable to a compact folded configuration wherein the holder stores elastic strain energy sufficient to unfold the holder from said compact folded configuration to said normal unfolded configuration, inserting said holder into said capsular bag through an incision in the eye and said anterior capsulotomy while the holder is in said compact folded configuration, and then implanting the holder in a fixed implanted position within said bag by releasing the folded holder within said bag to effect unfolding of the holder in the bag by said elastic strain energy to said normal unfolded configuration with the holder disposed in said fixed implanted position in said bag wherein said holder is located between said anterior capsular remnant and said posterior capsule of the bag, inserting said lens into said bag through said incision and said anterior capsulotomy, and mounting said lens on the unfolded implanted holder.

10. The method of claim 9 wherein:

said holder has normally anterior and posterior sides, and a space between said sides which is sized to receive said lens in a certain portion of said space wherein the lens does not project beyond said holder sides in the anterior/posterior direction of the holder, and light rays entering the eye can pass through the holder in said anterior/posterior direction, and said step of mounting said lens on said holder comprises mounting the lens on the holder with the lens located in said certain portion of said space.

11. The method of surgically implanting an intraocular lens in a patient's eye through an incision in the eye, comprising the steps of:

inserting said lens and a lens holder into the eye, implanting said lens holder in the eye, adjusting said lens relative to the implanted holder along the axis of the eye during surgery to focus said lens on the retina of the eye, and wherein said lens holder is a resilient foldable lens holder, said step of inserting said lens and lens holder into the eye comprises inserting said lens holder into the eye while the holder is in a compact folded configuration in which the holder stores elastic strain energy, effecting unfolding of the holder within said bag by said elastic strain energy to a normal configuration with the holder disposed in an implanted position in the eye, inserting said lens into the eye through said incision, and mounting said lens on the implanted lens holder, and said lens adjustment step comprises adjusting said lens relative to said holder after mounting of the lens on the holder.

12. The method of surgically implanting an intraocular lens in a patient's eye through an incision in the eye, comprising the steps of:

inserting said lens and a lens holder into the eye, implanting said lens holder in the eye, adjusting said lens bodily relative to the implanted holder along the axis of the eye during surgery without changing the shape of the lens to focus said lens on the retina of the eye, and wherein said lens is pivotally mounted on said holder for postoperative pivotal accommodation movement of the lens relative to said holder about a pivot axis transverse to said axis of the eye in response to tilting of the patient's head, and said step of adjusting said lens comprises retaining said lens in a fixed position about said pivot axis, adjusting said lens along said axis of the eye while said lens is in said fixed position about said pivot axis, and then permitting pivotal accommodation movement of the lens about said pivot axis after adjustment of the lens.

13. The method of implanting an intraocular lens in a patient's eye, comprising the steps of:

inserting a lens holder into the eye through an incision in the eye, implanting said lens holder in the eye in a fixed implanted position relative to the eye, inserting said lens into the eye through said incision, mounting said lens on said holder while said holder is in said implanted position in the eye, and adjusting said lens bodily relative to the implanted holder along the axis of the eye to focus said lens on the retina of the eye without changing either the shape of the lens or the position of the lens about said axis.

14. The method of implanting an intraocular lens in a patient's eye, comprising the steps of:

inserting a lens holder into the eye through an incision in the eye, implanting said lens holder in the eye in a fixed implanted position relative to the eye, inserting said lens into the eye through said incision, mounting said lens on said holder while said holder is in said implanted position in the eye, and wherein the patient's eye contains a capsular bag from which the natural lens matrix has been removed and which bag includes a posterior capsule and an anterior capsulotomy circumferentially surrounded by an anterior capsular remnant, said holder comprises a lens cage having a normally anterior ring and arcuate limbs extending posteriorly from said ring and forming with said ring a space within the cage which is sized to receive said lens in said space, and said step of implanting said holder in the eye comprises inserting said holder into said bag through said anterior capsulotomy and said incision and implanting the holder in said bag in said implanted position wherein said cage ring engages in the inner circumference of said bag and said cage limbs press against the posterior capsule of the bag, said step of mounting said lens on said holder comprises inserting the lens into said bag through said anterior capsulotomy and said incision and mounting the lens on said cage with the lens located within said space.

15. The method of claim 14, wherein:

said cage is resiliently foldable from a normal unfolded configuration wherein the cage forms said space to a compact folded configuration wherein said cage stores sufficient elastic strain energy to unfold the cage from said compact folded configuration to said normal unfolded configuration, said step of implanting said holder in said bag comprises inserting the cage into said bag through said anterior capsulotomy and said incision while the cage is in said compact folded configuration and then releasing the folded cage within the bag to effect unfolding of the cage within the bag from its compact folded configuration to its normal unfolded configuration by said elastic strain energy with the cage located in said implanted position, and said step of mounting said lens on said cage comprises inserting said lens into said cage space while said cage is in said implanted position, and mounting the lens on the cage with the lens located in said space.

16. The method of claim 15 including the additional step of:

adjusting said lens relative to said cage during surgery without changing the shape of the lens to focus said lens on the retina of the eye.

* * * * *